United States Patent [19]

Hallgren

[11] 4,377,706
[45] Mar. 22, 1983

[54] POLYALKOXYSILYLENOLETHERS

[75] Inventor: John E. Hallgren, Scotia, N.Y.

[73] Assignee: General Electric Company, Schenectady, N.Y.

[21] Appl. No.: 277,525

[22] Filed: Jun. 26, 1981

[51] Int. Cl.$^3$ ............................. C07F 7/18; C07F 7/04
[52] U.S. Cl. .................... 556/482; 556/470; 556/483; 556/485; 556/486
[58] Field of Search ............... 556/482, 483, 485, 486, 556/470

[56] References Cited

U.S. PATENT DOCUMENTS

| | | | |
|---|---|---|---|
| 3,299,173 | 1/1967 | Roselli | 556/483 X |
| 3,453,307 | 7/1969 | Nitzsche et al. | 556/470 X |
| 3,472,888 | 10/1969 | Bazouin | 556/470 |
| 4,294,975 | 10/1981 | Takago et al. | 556/482 |

FOREIGN PATENT DOCUMENTS

| | | | |
|---|---|---|---|
| 1044448 | 9/1966 | United Kingdom | 556/470 |
| 119181 | 2/1958 | U.S.S.R. | 556/470 |
| 119186 | 2/1958 | U.S.S.R. | 556/470 |

*Primary Examiner*—Paul F. Shaver
*Attorney, Agent, or Firm*—William A. Teoli; James C. Davis, Jr.; James Magee, Jr.

[57] ABSTRACT

Polyalkoxysilylenolethers, for example, methyldimethoxyisopropenoxysilane, are provided and a method for making such silanes. The dialkoxysilylenolethers can be used as end-capping silanes for making noncorrosive RTV compositions.

8 Claims, No Drawings

POLYALKOXYSILYLENOLETHERS

CROSS REFERENCE TO RELATED APPLICATIONS

Reference is made to copending application RD-13275, of Mary Ann White, Melvin D. Beers, Gary M. Lucas, Robert A. Smith and Roger T. Swiger, for One Package, Stable, Moisture Curable, Polyalkoxy-Terminated Organopolysiloxane Compositions and Method for Making.

BACKGROUND OF THE INVENTION

The present invention relates to polyalkoxysilylenolethers, for example, methyldimethoxyisopropenoxysilane and a method for making such materials. More particularly, the present invention relates to the preparation of methyldimethoxyisopropenoxysilane by initially forming methyldimethoxysilane from methyldichlorosilane and methanol and thereafter converting the methyldimethoxysilane by reacting it with acetone in the presence of a transition metal catalyst.

As shown in the copending application of White et al. RD-13275, filed concurrently herewith and assigned to the same assignee as the present invention, methyldimethoxyisopropenoxysilane can be used as a scavenging silane for hydroxy functional groups to prepare room temperature vulcanizing compositions under substantially anhydrous conditions with a mixture of a silanol-terminated polydiorganosiloxane and fumed silica filler. Silylenolethers have been prepared, usually from ketones and chlorosilanes, in the presence of bases, as shown by H. O. House et al, Journal of Organic Chemistry, 34, 2324 (1969). Additional procedures are shown by H. Sakurai et al, Tetrahedron Letters, 31, 2671 (1971) and R. Calas, Journal of Organometallic Chemistry, 200, 11 (1980), utilizing ketones and silicon hydrides in the presence of a variety of transition metal catalysts.

The present invention is based on the discovery that polyalkoxysilylenolethers of the formula,

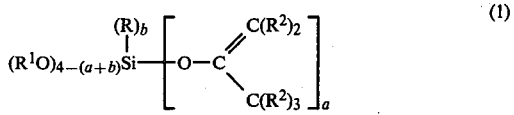

can be made by heating the corresponding polyalkoxysilane and ketone in the presence of a transition metal catalyst, where R is a $C_{(1-13)}$ substituted or unsubstituted monovalent hydrocarbon radical, $R^1$ is a $C_{(1-8)}$ alkyl radical, $R^2$ is selected from hydrogen, $R^1$ radicals and mixtures thereof, a is equal to 1 or 2, b is equal to 0 or 1, and the sum of a+b is equal to 1 or 2.

STATEMENT OF THE INVENTION

There is provided by the present invention, a method for making polyalkoxysilylenolethers of formula (1) which comprises, (1) heating a mixture of polyalkoxysilane of the formula,

and a ketone of the formula,

in the presence of an effective amount of a transition metal catalyst and (2) recovering the polyalkoxysilylenolether from the mixture of (1), where R, $R^1$, $R^2$, a and b are as previously defined.

Radicals included within R of formula (1) are, for example, $C_{(1-8)}$ alkyl radicals, for example, methyl, ethyl, vinyl, propyl, butyl, pentyl, etc.; $C_{(6-13)}$ aryl radicals, for example, phenyl, xylyl, tolyl, napthyl, etc., halogenated derivatives thereof, for example, trifluoropropyl, chlorophenyl, etc. Radicals included within $R^1$ are, for example, $C_{(1-8)}$ alkyl radicals, for example, methyl, ethyl, propyl, butyl, etc. Radicals included within $R^2$ are, for example, hydrogen, and the aforementioned $R^1$ radicals. In formula (1) where $R^1$ and $R^2$ can be more than one radical, these radicals can be the same or different.

There are included by the polyalkoxysilylenolethers of formula (1) compounds such as methyldimethoxyisopropenoxysilane, hexyldimethoxyisopropenoxysilane, methyldiethoxyisopropenoxysilane, phenyldimethoxyisopropenoxysilane, methyldimethoxy-2-butenoxysilane.

Some of the polyalkoxysilanes which are included within formula (2) are, for example, methyldimethoxysilane, hexyldimethoxysilane, phenyldimethoxysilane, dimethylmethoxysilane, methyldiethoxysilane, methyldipropoxysilane, methyl-bis(2-methoxyethoxy)silane, trimethoxysilane, triethoxysilane, dimethoxysilane, diethoxysilane.

Included within the ketones shown by formula (3) are, for example, acetone, methylethylketone, diethylketone, acetophenone, cyclohexanone, benzophenone, 2-pentanone.

The transition metal catalysts which can be utilized in the practice of the present invention include, for example, cobalt carbonyl catalysts, such as $Co_2(CO)_8$/pyridine.

In addition, there can be used a nickel metal thiophenol catalyst. Other nickel catalysts can be employed resulting from the use of nickel compounds for example, nickel nitrate, nickel chloride, and nickel acetate which can be contacted with a mercaptan, $R^3SH$, where $R^3$ is a $C_{(1-8)}$ alkyl radical, or a thiophenol, $R^4SH$, where $R^4$ is a $C_{(6-13)}$ monovalent aryl radical, where sufficient sulfur compound is used to provide at least two atoms of sulfur, per atom of nickel.

A typical nickel metal-thiophenol preparation involves the use of anhydrous nickel chloride and triethylsilane utilizing a minor amount of chloroplatinic acid which can be added to the nickel chloride triethylsilane mixture after it has been brought to reflux to which an aryl thiol is added. An additional catalyst which can be used is nickel bis(thiophenoxide), which can be prepared by the method of Peach, J. Inorg. Nucl. Chem., 41 11390, (1979).

The above nickel-sulfur compound catalysts can be supported on various substrates, for example, alumina, silica, etc.

In the practice of the invention, the preferred procedure is to effect contact between the polyalkoxysilane of formula (2) and the ketone of formula (3) in the presence of an effective amount of the transition metal catalyst. It has been found that the transition metal catalyst can be utilized at from 0.001% to 10% by weight of transition metal based on the weight of the reaction mixture consisting of the polyalkoxysilane of formula (2) and the ketone of formula (3) along with optionally a substantially inert organic solvent to facilitate the reaction. Suitable organic solvents which can be used along with the polyalkoxysilane and the ketone at temperatures in the range of from 25° to 250° C. with agitation, such as stirring, are, for example, methylene chloride, chlorobenzene, toluene, hexane, ether, THF, etc.

A particularly preferred procedure is to produce the polyalkoxysilane of formula (2) by reacting the corresponding chlorosilane and alcohol in a hot tube at a temperature of 90° C. to 100° C. in accordance with the following equation,

$$(X)_{4-(a+b)}Si(H)_a + YR^1OH \longrightarrow \text{formula (2)},$$

where X is halogen, and R, $R^1$, a and b are as previously defined, and Y is a positive integer, followed by the reaction of polyalkoxysilane with the ketone as previously defined. In making the polyalkoxysilane of formula (2) in accordance with the above equation, there should be used at least 1 mole $R^1OH$ per mole of X in the chlorosilane.

In order that those skilled in the art will be better able to practice the present invention, the following examples are given by way of illustration and not by way of limitation. All parts are by weight unless otherwise indicated.

EXAMPLE 1

A mixture was refluxed under a nitrogen atmosphere for 9 hours consisting of 3.18 parts of dimethoxymethylsilane, 2.9 parts of acetone, 58 parts of methylene chloride and 1.4 parts of a 10% solution of cobalt carbonyl in orthodichlorobenzene. There was obtained an 83% yield of methyldimethoxyisopropenoxysilane having the formula,

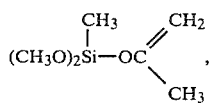

based on gas chromatographic analysis.

EXAMPLE 2

A nickel metal catalyst was prepared by refluxing a mixture for 1 hour under nitrogen with stirring consisting of one part of anhydrous nickel chloride, 10 parts of triethylsilane, which had been initially warmed to reflux, followed by the addition of a tiny crystal of $H_2PtCl_6$. The mixture immediately turned black upon addition of the hexachloro platinum compound. After the 1 hour reflux period, the nickel metal catalyst was recovered by filtration under nitrogen and washed twice with 20 parts of methylene chloride and dried in vacuo.

A mixture was warmed to about 80° C. for 3 hours consisting of the above nickel metal catalyst, 3.18 parts of methyldimethoxysilane, 3.5 parts of acetone and 0.011 part of thiophenol. Upon allowing the mixture to cool, it was analyzed with a gas chromatograph. Based on method of preparation, and gas chromatography, there was obtained a 73% yield or 3.5 parts of methyldimethoxyisopropenoxysilane of Example 1.

EXAMPLE 3

A 22 ml Hastelloy-C pressure reactor was charged with 5.0 g (42.2 mmol) of $MeSi(H)(OMe)_2$, 5.0 g (86.2 mmol) of acetone, 0.5 g of dodecane as internal standard and 0.0051 g (18.4 μmol) of $Ni(SC_6H_5)_2$. The reactor was sealed, then warmed to 155° C. for 20 minutes. Upon cooling and venting, gc showed the presence of 5.73 g (75%) of methyldimethoxyisopropenoxysilane, 0.76 g (10%) of methyldimethoyisopropoxy silane, and 0.64 g methyltrimethoxysilane. The catalyst was recovered by filtration, and a fresh charge of silane and acetone added. After an identical reaction, 6.81 g (89%) of methyldimethoxyisopropenoxysilane was detected.

Four parts of the above methyldimethoxyisopropenoxysilane is mixed with 85 parts of a silanol-terminated polydimethylsiloxane having a viscosity of about 2500 centipoises and 0.9% by weight of hydroxy radicals and 17 parts of octamethylcyclotetrasiloxane treated fumed silica filler under a nitrogen atmosphere. There is then added to the mixture, 0.4 part of trimethoxysilylpropyltetramethylguanidine in 0.23 part of dibutyltindiacetate. The resulting room temperature vulcanizing formulation is allowed to shelf age up to 2 days at temperatures of 50° and 100° C. to determine its tack-free time in minutes. The following results are obtained:

| Shelf Age | Enoxy TFT (Min) | | |
|---|---|---|---|
| (days) | RT | 50° C. | 100° C. |
| 0 | 65 | — | |
| 1 | 65 | | 70 |
| 2 | 65 | | 90 |

The above results show that the methyldimethoxyisopropenoxysilane can be used as an endcapping silane to provide for room temperature vulcanizing compositions.

EXAMPLE 4

The 22 ml Hastelloy-C pressure reactor of Example 3 was charged with 0.056 g (0.12 mol) of $Ni(SC_{12}H_{25})_2$, 5.0 g (47.2 mmol) of methyldimethoxysilane, 5.0 g (86.2 mmol) of acetone, and 0.5 g of dodecane as internal standard. The mixture was warmed to 130° C. and maintained at that temperature for 0.5 hours. After cooling, and venting off the hydrogen gas formed during the course of the reaction, gc analysis showed the presence of 1.12 g (22%) of starting methyldimethoxysilane, 0.85 g (13%) of methyltrimethoxysilane, 1.27 g (17%) of methyldimethoxyisopropoxy silane, and 3.64 g or a 62% yield of methyldimethoxyisopropenoxysilane.

EXAMPLE 5

To a 500 ml round bottom flask, 100 g of ⅛" alumina tablets were soaked in 100 ml of a 10% solution of $Ni(SC_6H_5)_2$ in concentrated aqueous ammonia for 4 hours. Ammonia was then removed under reduced pressure until catalyst just began to precipitate. The solution was decanted from the pellets and the pellets washed repeatedly with water followed by ethanol and ether, finally dried in vacuo at 100° C. overnight.

The procedure of Example 3 was repeated except that in place of $Ni(SC_6H_5)_2$, the above $Ni(SC_6H_5)_2$ soaked alumina tablets were used as the transition metal catalyst. In addition, further reactions were run with Ni(SC$_6$H$_5$)$_2$ on other substrates, for example, alumina pellets post treated by washing with a 1% aqueous solution of H$_3$PO$_4$, 3 A molecular sieves, silica and a silica-alumina substrate. The following results were obtained, where % Conversion means the amount of mixture changed in the reaction and % Enoxysilane means the yield of the methyldimethoxyisopropenoxysilane in the converted mixture:

| Substrate | % Conversion | % Enoxysilane |
|---|---|---|
| Al$_2$O$_3$ | 83 | 63 |
| Al$_2$O$_3$ | 77 | 73 |
| 3A molecular sieves | 13 | 67 |
| Silica | 50 | 47 |
| Silica-alumina | 28 | 85 |

The above results show that aluminum oxide is a superior substrate for converting the reaction mixture to various reaction products, while the silica-alumina catalyst is selective for the production of methyldimethoxyisopropenoxysilane.

Although the above examples are directed to only a few of the very many variables which can be used in the practice of the present invention, it should be understood that the present invention is directed to a much broader variety of polyalkoxysilanes, ketones and transition metal catalysts which can be used to make a wide variety of polyalkoxysilanes as shown by formula (1).

What I claim as new and desire to secure by Letters Patent of the United States is:

1. Methyldimethoxyisopropenoxysilane.
2. A method for making polyalkoxysilylenolethers which comprises,
   (1) heating a mixture of a polyalkoxysilane of the formula,

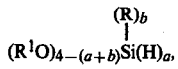
   $(R^1O)_{4-(a+b)}Si(H)_a,$ and a ketone selected from the class consisting of acetone, methylethylketone, diethylketone, acetophenone, cyclohexanone, benzophenone and 2-pentaneone in the presence of an effective amount of a transition metal catalyst and
   (2) recovering the resulting polyalkoxysilylenolether from the mixture of (1), where R is a C$_{(1-13)}$ substituted or unsubstituted monovalent hydrocarbon radicals, R$^1$ is a C$_{(1-8)}$ alkyl radical, a is an integer equal to 1 or 2, b is an integer equal to 0 or 1, and the sum of a+b is equal to 1 or 2.
3. A method for making polyalkoxysilylenolether which comprises,
   (1) effecting reaction at a temperature in the range of from 20° C. to 250° C. of a polyhalosilane having the formula,

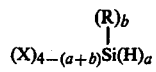
   $(X)_{4-(a+b)}Si(H)_a$ and an alkanol having the formula,

   R$^1$OH to produce a polyalkoxysilane having the formula,

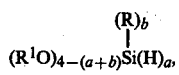
   $(R^1O)_{4-(a+b)}Si(H)_a,$ (2) effecting reaction between the polyalkoxysilane of (1) and a ketone selected from the class consisting of acetone, methylethylketone, diethylketone, acetophenone, cyclohexanone, benzophenone and 2-pentaneone at a temperature in the range of between 20° C. to 250° C. in the presence of an effective amount of a transition metal catalyst and
   (3) recovering the polyalkoxysilylenolether from the mixture of (2), where X is halogen, where R is a C$_{(1-13)}$ substituted or unsubstituted monovalent hydrocarbon radicals, R$^1$ is a C$_{(1-8)}$ alkyl radical, a is an integer equal to 1 or 2, b is an integer equal to 0 or 1, and the sum of a+b is equal to 1 or 2.
4. A method in accordance with claim 2, where the transition metal catalyst is a cobalt carbonylpyridine catalyst.
5. A method in accordance with claim 2, where the transition metal catalyst is a nickel metal catalyst, promoted with thiophenol.
6. A method in accordance with claim 2, where the transition metal catalyst is nickel bis(thiophenoxide).
7. A method in accordance with claim 2, where the polyalkoxysilane is methyldimethoxysilane.
8. A method in accordance with claim 2, where the ketone is acetone.

* * * * *